United States Patent [19]

Gall

[11]  4,404,387
[45]  Sep. 13, 1983

[54] AMINOALKYL-SUBSTITUTED IMIDAZOLES

[75] Inventor: Martin Gall, Kalamazoo, Mich.

[73] Assignee: The Upjohn Company, Kalamazoo, Mich.

[21] Appl. No.: 362,446

[22] Filed: Mar. 26, 1982

Related U.S. Application Data

[62] Division of Ser. No. 187,920, Sep. 17, 1980, Pat. No. 4,338,453.

[51] Int. Cl.³ .................. C07D 233/54; C07D 403/08; A61K 31/445

[52] U.S. Cl. .................................. 546/193; 546/210; 548/336; 548/333; 548/262; 548/263; 424/267; 424/273 R; 544/366

[58] Field of Search ................ 548/336; 546/193, 210

[56] References Cited

U.S. PATENT DOCUMENTS 3,927,011  12/1975  Nakanishi et al. .................. 548/336

Primary Examiner—Donald G. Daus
Assistant Examiner—S. A. Gibson
Attorney, Agent, or Firm—Lawrence T. Welch

[57] ABSTRACT

The present invention provides certain substituted-piperazinyl-1,2,4-triazoles which are useful for the treatment of sensitized humans for allergies and anaphylactic reactions.

13 Claims, No Drawings

AMINOALKYL-SUBSTITUTED IMIDAZOLES

CROSS REFERENCE TO RELATED APPLICATION

This application is a divisional of copending application Ser. No. 187,920, filed Sept. 17, 1980, now issued as U.S. Pat. No. 4,338,453.

BACKGROUND OF THE INVENTION

The present invention relates to novel substituted imidazoles. Most particularly, the present invention relates to certain aminoalkyl substituted imidazols. The pharmaceutical use and preparation of these compounds is described in U.S. Pat. No. 4,338,453, which is expressly incorporated herein by reference.

PRIOR ART

Various imidazoles are known. These compounds have been described as useful for a wide range of uses. Known imidazole compounds include 1,2,4,5-tetra-substituted imidazoles useful as antitumor, antiviral, antiinflammatory agent agents, and as protective agents against cerebral anoxia or hypoxia such as are described in British Pat. No. 2,016,011 (abstracted in Derwent Farmdoc CPI No. 68606B/38), French Pat. No. 2,132,632 (abstracted in Derwent Farmdoc CPI No. 10105U-B), U.S. Pat. No. 3,651,080, and Belgian Pat. No. 810,117 (abstracted in Farmdoc CPI No. 41717V/23); 1-substituted imidazoles for use in treating inflammation, hypertension, thrombosis and asthma such as described in Japanese Patent Application No. 109974 (abstracted in Derwent Farmdoc CPI No. 72897B/40); 1,2-di-substituted-4-haloimidazoles-5-acetic acid derivatives for use as diuretics and hypotensives, as described in U.S. Pat. No. 4,207,324; and 1,4,5-trisubstituted imidazoles useful as antiallergic and hypotensive agents such as described in British Pat. No. 1,134,580. U.S. Pat. No. 3,505,350 discloses certain mercapto imidazole derivatives which are useful an antiinflammatory agents.

SUMMARY OF THE INVENTION

The present invention particularly provides a compound according to Formula I

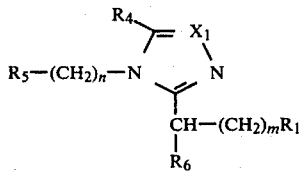

or a pharmacologically acceptable salt thereof,
wherein $X_1$ is
(a) $=CH-$; or
(b) $=C(CH_3)-$;
wherein m is zero, one, 2 or 3;
wherein n is zero, one or 2,
wherein $R_1$ is:
(a) 1-piperidinyl substituted at the 3 or 4 position by $R_{15}$, wherein $R_{15}$ is defined as below;
(b) $-N(CH_3)-(CH_2)_p-R_{15}$, wherein $R_{15}$ and p are as defined below; or
(c) $-NH-(CH_2)_p-R_{15}$, wherein p is 1, 2, or 3 and $R_{15}$ is as defined below;
wherein $R_4$ is:
(a) hydrogen;
(b) alkyl of one to three carbon atoms, inclusive;
(c) $R_{54}OCH_2-$, wherein $R_{54}$ is defined below;
(d) $-CH(R_{35})(OH)$; or
(e) $-R_{35}$;
wherein $R_5$, $R_{15}$, $R_{25}$ and $R_{35}$ are the same or different and are
(i) 2,3, or 4 pyridinyl, or
(ii) phenyl substituted by zero to 2 chloro, fluoro, bromo, alkyl of from one to 3 carbon atoms, or alkoxy of from one to 3 carbon atoms, or
(iii) phenyl substituted by one trifluoromethyl and zero to one of the previous phenyl substituents,
wherein $R_6$ is:
(a) hydrogen;
(b) $-OR_{54}$;
(c) alkanoyloxy of from one to 3 carbon atoms; or
(d) alkyl of from one to 3 carbon atoms; with the proviso that when m is zero, $R_6$ does not contain oxygen;
wherein $R_{17}$ is methyl, phenyl, benzyl, or 2-phenylethyl; and
wherein $R_{54}$ is hydrogen or alkyl of one to 3 carbon atoms;
or an enantiomer (when $R_4$ is $-CH(R_{35})OH$ or when $R_6$ is not hydrogen) or diastereomer (when $R_4$ is $-CH(R_{35})OH$ and $R_6$ is not hydrogen) of such compound.

DESCRIPTION OF THE PREFERRED EMBODIMENTS

The present invention particularly provides:
5-Methyl-1-phenyl-N-(2-phenylethyl)-1H-imidazole-ethaneamine;
N-5-Dimethyl-1-phenyl-N-(2-phenylethyl)-1H-imidazole-ethaneamine; and
1-(4-Fluorophenyl)-5-methyl-N-(2-phenylethyl)-1H-imidazole-2-ethaneamine.

I claim:
1. A compound according to formula I

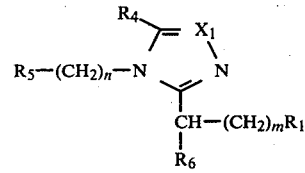

or a pharmacologically acceptable salt thereof,
wherein $X_1$ is
(a) $=CH-$; or
(b) $=C(CH_3)-$;
wherein m is zero, one, 2 or 3;
wherein n is zero, one or 2,
wherein $R_1$ is:
(a) 1-piperidinyl substituted at the 3 or 4 position by $R_{15}$, wherein $R_{15}$ is defined as below;
(b) $-N(CH_3)-(CH_2)_p-R_{15}$, wherein $R_{15}$ and p are as defined below; or
(c) $-NH-(CH_2)_p-R_{15}$, wherein p is 1, 2, or 3 and $R_{15}$ is as defined below;
wherein $R_4$ is:
(a) hydrogen;
(b) alkyl of one to three carbon atoms, inclusive;
(c) $R_{54}OCH_2-$, wherein $R_{54}$ is defined below;
(d) $-CH(R_{35})(OH)$; or (e) —$R_{35}$;

wherein $R_5$, $R_{15}$, $R_{25}$ and $R_{35}$ are the same or different and are
- (i) 2,3, or 4 pyridinyl, or
- (ii) phenyl substituted by zero to 2 chloro, fluoro, bromo, alkyl of from one to 3 carbon atoms, or alkoxy of from one to 3 carbon atoms, or
- (iii) phenyl substituted by one trifluoromethyl and zero to one of the previous phenyl substituents, wherein $R_6$ is:
- (a) hydrogen;
- (b) —$OR_{54}$;
- (c) alkanoyloxy of from one to 3 carbon atoms; or
- (d) alkyl of from one to 3 cabon atoms; with the proviso that when m is zero, $R_6$ does not contain oxygen;

wherein $R_{17}$ is methyl, phenyl, benzyl, or 2-phenylethyl; and wherein $R_{54}$ is hydrogen or alkyl of one to 3 carbon atoms;

or an enantiomer (when $R_4$ is —$CH(R_{35})OH$ or when $R_6$ is not hydrogen) or diastereomer (when $R_4$ is —$CH(R_{35})OH$ and $R_6$ is not hydrogen) of such compound.

2. A compound of claim 1, wherein n is zero and $R_6$ is hydrogen.

3. A compound of claim 2, wherein m is 2.

4. A compound of claim 2, wherein m is one or 2, and $R_4$ is hydrogen, methyl, hydroxymethyl, or —$CH(R_{35})(OH)$, wherein $R_5$ and $R_{35}$ are phenyl substituted by zero to 2 chloro, fluoro or bromo.

5. 5-Methyl-1-phenyl-N-(2-phenylethyl)-1H-imidazole-ethaneamine, a compound of claim 4.

6. N,5-Dimethyl-1-phenyl-N-(2-phenylethyl)-1H-imidazole-ethaneamine, a compound of claim 4.

7. A compound of claim 4, wherein $R_4$ is methyl.

8. 1-(4-Fluorophenyl)-5-methyl-N-(2-phenylethyl)-1H-imidazole-2-ethaneamine, a compound of claim 7.

9. A compound of claim 1, wherein $X_1$ is =CH—.

10. A compound of claim 1, wherein $X_1$ is =C(CH$_3$)—.

11. A compound of claim 1, wherein $R_4$ is hydrogen.

12. A compound of claim 4, wherein $R_6$ is hydrogen.

13. A compound of claim 1, wherein $R_4$ is methyl or thiomethyl.

* * * * *

UNITED STATES PATENT AND TRADEMARK OFFICE
CERTIFICATE OF CORRECTION

PATENT NO. : 4,404,387
DATED : 13 September 1983
INVENTOR(S) : Martin Gall

It is certified that error appears in the above—identified patent and that said Letters Patent are hereby corrected as shown below:

Column 4, lines 22-23, "is methyl or thiomethyl." should read -- is methyl. --

Signed and Sealed this

Seventeenth Day of April 1984

[SEAL]

Attest:

GERALD J. MOSSINGHOFF

Attesting Officer  Commissioner of Patents and Trademarks